United States Patent [19]

Smole

[11] Patent Number: 4,832,063
[45] Date of Patent: May 23, 1989

[54] FLOSSING DEVICE

[76] Inventor: Frederick T. Smole, 721 E. Lick Rd., P.O. Box 766, McCall, Id. 83638

[21] Appl. No.: 106,350

[22] Filed: Oct. 9, 1987

[51] Int. Cl.[4] ............................................. A61C 15/00
[52] U.S. Cl. ................................... 132/329; 132/321; 223/102
[58] Field of Search ............................ 132/89, 91, 93; 433/148; 223/102; 156/158

[56] References Cited

U.S. PATENT DOCUMENTS

| 342,725 | 5/1886 | Arnold | 223/102 |
| 1,285,988 | 11/1918 | Gudebrod | 132/89 |
| 1,839,486 | 1/1932 | Lawton | 132/93 |
| 1,863,717 | 6/1932 | Holden | 223/102 |
| 2,522,794 | 9/1950 | Medof | 132/93 |
| 2,612,177 | 9/1952 | Footer | 132/93 |
| 4,133,339 | 1/1979 | Naslund | 132/89 |
| 4,364,380 | 12/1982 | Lewis | 132/91 |
| 4,465,462 | 8/1984 | Ticknor | 132/93 |

Primary Examiner—John J. Wilson
Attorney, Agent, or Firm—Paul F. Horton

[57] ABSTRACT

A flossing device to floss bacterial plaque off tooth structures, including teeth and osseous implanted abutments, said flossing device comprising a leader with affixed cord. The leader is provided with a hook portion, preferably formed by and integral with the leader; the leader being bent back upon itself at an acute angle which permits ready insertion of the leader between adjacent tooth structures and which permits ready access to the leader as the free end of the hook effectively hooks about the tooth structure and extends outward of the tooth structure for convenient grasping by the user, upon retraction of the leader. The terminal free end of the hook may be enlarged and blunted for secure grasping. The flossing cord is singular, being constructed of a multiplicity of braided strands for entrapment and removal of plaque from the tooth structures.

7 Claims, 1 Drawing Sheet

FLOSSING DEVICE

BACKGROUND OF THE INVENTION

1. Field of the Invention

This invention relates, in general, to devices for use in dental hygiene, and, more particularly, to flossing devices used for flossing teeth and implanted metal abutments.

2. Description of the Prior Art

Flossing of the teeth and flossing of abutments, in the case of individuals having an osseous integrated implant with fixed bridge, is very important in the maintenance of dental hygiene in that flossing prevents the build-up of bacterial plaque—a common cause of peridontal disease.

For the flossing of teeth, common dental floss in the form of a single strand or fiber, often waxed, is widely known and used. Such floss is often difficult to insert between adjacent teeth because the crowns of the teeth are often in close apposition on one another, often resulting in a severing of the floss or, on occasion, causing injury to the underlying gum when the gum is contacted by the floss under extreme tension. Additionally, once in place, the floss must be maneuvered in a difficult up and down direction for proper flossing.

In attempting to overcome these problems, leaders have been employed for assistance in insertion of the floss and multi-stranded and textured cords have been utilized for more thorough cleansing. A flossing system developed by L. Thomas et al, U.S. Pat. No. 4,215,478, includes a leader to which is attached a "mop" portion; the mop being held in place by an eye or slot in the leader. The Thomas device requires a leader which is doubled in the form of a loop to form the eye land also requires a doubling of the mop in its placement through the eye and therefore is too massive for convenient use with teeth. Further, the Thomas device makes grasping of the leader difficult in that the leader must be grasped within the mouth when inserted from exterior the teeth. T. Thornton, U.S. Pat. No. 3,896,824, provides a teeth cleaner having a leader or string portion which is inserted past the contact point of crowns of adjacent teeth in conventional manner and a brush portion for rubbing against the teeth. U.S. Pat. No 4,519,408, issued to N. Charatan, utilizes a housing and flossing portion; the flossing portion being inserted between adjacent teeth in conventional fashion.

Where an individual has been provided with an osseous integrated implant with a fixed bridge, laterally spaced, rod shaped abutments, usually made of titanium, are implanted in the bone and extend parallel to one another up through the gum for attachment of the fixed bridge. The abutments are subject to bacterial plaque and the bridge, being continuous across the abutments prevents floss from being inserted in the conventional manner. No flossing device or system is known which permits insertion of floss between abutments and permits grasping of the flossing device exterior of the abutments.

SUMMARY OF THE INVENTION

The present invention overcomes the problems of floss insertion between teeth having wedged crowns and abutments with fixed bridges by providing a flossing device which includes a single, monofilament leader having a hook structure which enables insertion of the leader between teeth or abutments, herein referred to as "tooth structures", and which is retractable, once inserted, to a position partially encircling the tooth structure whereby the leader may be grasped exterior of the tooth structure. The problem of inadequate cleaning because the use of a single floss strand or because of doubled floss cords and doubled leaders is also overcome by the provision of a single floss cord, having a multiplicity of braided strands for entrapment and removal of the plaque, and by the use of a tubular floss cord in which the leader is received and affixed by vinyl cement. Additional objects and advantages will become apparent and a more thorough and comprehensive understanding may be had from the following description taken in conjunction with the accompanying drawings forming a part of this specification.

DETAILED DESCRIPTION OF THE INVENTION

Figure 1:
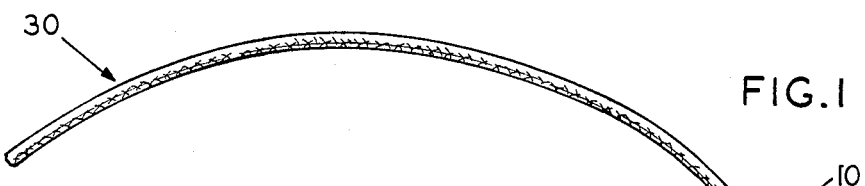
FIG. 1 is a perspective view of a flossing device made according to the present invention.
Figure 2:
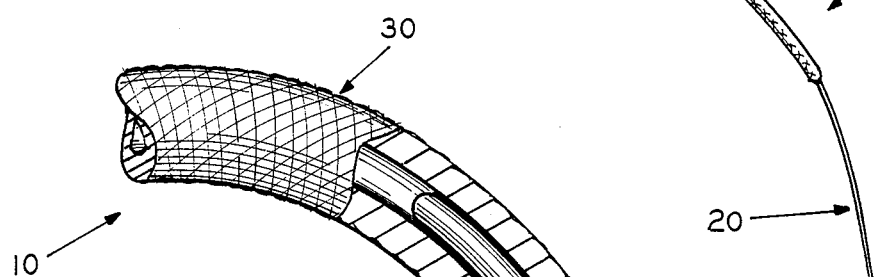
FIG. 2 is an enlarged perspective view of the flossing device, in partial section, showing joinder of the monofilament leader with the single, braided cord.

Referring now to the drawings, and to FIGS. 1 and 2, in particular, an embodiment to be preferred of a flossing device 10, made according to the present invention is disclosed. Flossing device 10 includes a leader portion 20 and a cord portion 30.

Leader 20 is in the form of a single, resilient, monofilament line, preferably composed of nylon. The line, from which the leader is constructed, may be of any suitable diameter and is circular in cross section, having a smooth outer surface, free from slots, eyes, or other openings, for hygienic reasons as well as to prevent the leader from catching on tooth structures or the gums. A single, monofilament line assures any unraveling of the leader and also reduces bulk. Leader 20 is provided with a hook member 22 which may be integral with the remainder of the leader. In this, the preferred embodiment, the leader is bent back upon itself at an acute angle to define a hook having a relatively pointed leading end portion 21, at the bend, and a trailing leg 23, approximately one inch in length. Leg 23 may include a blunt tip 24 for manual grasping, as will hereinafter be explained. The bend in the leader to define the hook is made possible by heat treating the nylon, causing the nylon to retain the form desired so that the leg remains at substantially the same angle relative to the main shaft 25 of the leader. Blunt tip 24 may also be formed by heat treatment, by molding, or otherwise.

Connected to leader 20 is a single flossing cord 30. Cord 30 may be constructed of any suitable material, waxed or unwaxed. In the preferred embodiment the cord is made of a multiplicity of braided nylon strands in the form of a tube. The cord, being singular, prevents any intertwining with other cords, and, in being composed of a multiplicity of strands, provides a large number of contact surfaces as well as recesses between strands for the entrapment and removal of bacterial plaque from the tooth structures. Cord 30, in being tubular, permits a convenient insertion of leader 20 into the cord without an appreciable expansion of the cord at the juncture. In that the leader is used to pull the cord between teeth or other tooth structures, it is important that the width of the cord at the leader junction be held to a minimum. Vinyl cement is used to hold the leader within the cord to provide a flexible joinder.

Figure 3:
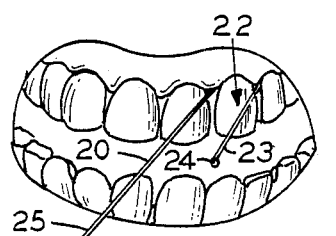
FIG. 3 is a perspective view showing placement of the leader about a tooth.
Figure 4:
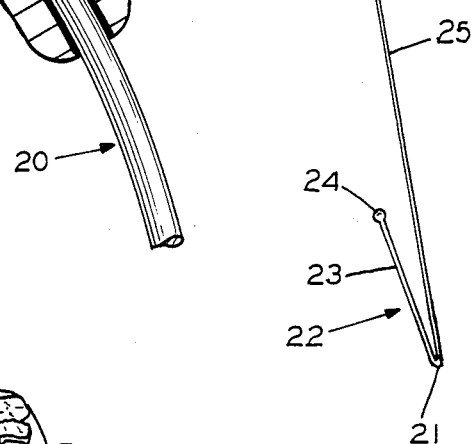
FIG. 4 is a perspective view showing placement of the leader about in implanted abutment.
Figure 4:
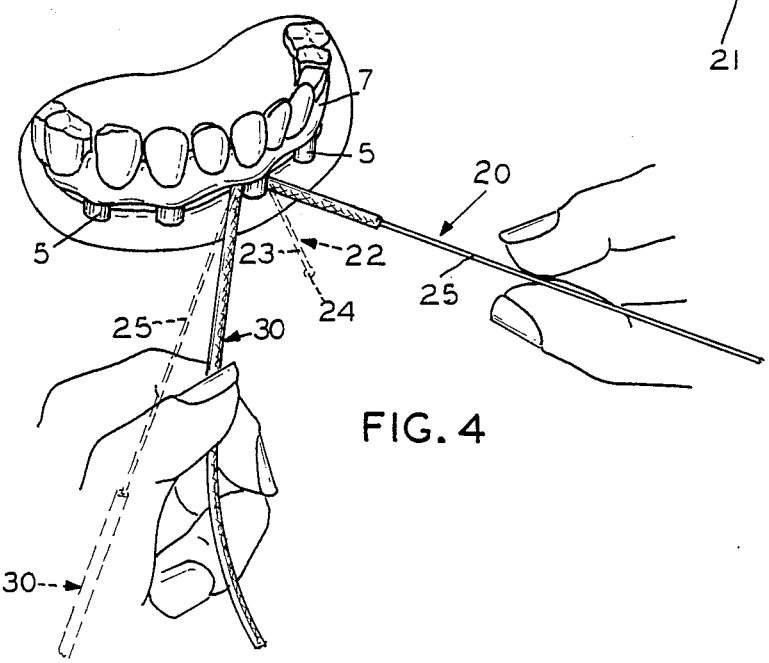

Referring now to FIG. 3, use of flossing device 10 for the flossing of teeth will be described. With all known flossing devices, the flossing cord must be pulled either upward or downward, as the case may be, between often contacting crowns of adjacent teeth, or, where leaders are provided, the leader is inserted in one direction and must be grasped on the opposite side of the teeth from where inserted. That is, when inserted externally of the teeth, the leader must be grasped within the mouth cavity as defined by the teeth. In using the device of the present invention, leader 20 may be inserted between adjacent teeth, below the crowns, with leading portion 21 first being inserted. Once trailing leg 23 of hook 22 has been completely received within the mouth cavity, the leader is retracted so that blunt tip 24 of the leader hook emerges between the teeth so that the hook partially encircles the tooth. Blunt tip 24 of the leader hook is then grasped and pulled outwardly until cord 30 engages the sides and back of the tooth. Device 10 is then moved back and forth in a reciprocating, shoeshine, manner for flossing the tooth. The procedure is repeated for each tooth.

Where the individual has an osseous integrated implant, utilizing, for example, titanium abutments 5 and a fixed bridge 7, as shown in FIG. 4, it is obvious that the only way that the abutments may be flossed is by insertion of the flossing device between adjacent abutments in that the fixed bridge prevents vertical insertion. Leading end portion 21 is first inserted between the tooth structures, abutments 5, and insertion continues until the hook is placed inward of the abutments within the mouth cavity. Leg 23, being bent at an acute angle, i.e., at an angle less than ninety degrees, and preferably at an angle approximating forty five degrees, relative to shaft 25 of the leader, is then pulled back on the other side of the abutment by retraction of the leader. The small blunt tip 24 of the leader is then grasped and the cord 30 pulled into position for flossing of the abutment. The process is repeated until all abutments are clean. After use, device 10 is cleansed thoroughly and allowed to dry for future use.

Having thus described in detail a preferred embodiment of the present invention, it is to be appreciated and will be apparent to those skilled in the art that other physical changes could be made in the device without altering the inventive concepts and principles embodied therein. The present embodiment is therefore to be considered in all respects as illustrative and not restrictive, the scope of the invention being indicated by the appended claims rather than by the foregoing description, and all changes which come within the meaning and range of equivalency of the claims are therefore to be embraced therein.

I claim:

1. A flossing device comprising:
    a single floss leader for insertion between tooth structures, said leader provided with a fixed resilient hook member formed from an acute angle bend in said leader for threading said leader behind a tooth structure to partially encircle the tooth structure and for retrieving said leader from a position forward of the tooth structure; and
    a single elongated flossing cord connected to and integral with said leader, said cord having a multiplicity of braided strands for trapping and removing plaque from the tooth structures.

2. The device as described in claim 1 wherein said floss leader and said flossing cord are constructed of nylon.

3. The device as described in claim 1 wherein the terminal end of said hook is provided with grasping means.

4. A flossing device comprising:
    a single, elongated, resilient, monofilament floss leader, one end of which is bent back upon itself at an acute angle to define a fixed hook for threading the leader behind a tooth structure to partially encircle the tooth structure and for retrieving said leader from a position forward of the tooth structure; and
    a single, elongated flossing cord connected to said leader, said cord comprising a multiplicity of braided strands for trapping and removing plaque from the tooth structure.

5. The flossing device as described in claim 4 wherein the hook includes a pointed forward portion at the bend for insertion of the leader between tooth structures and a blunt grasping member at its terminal end for manual grasping of the leader.

6. The flossing device as described in claim 4 wherein said cord is tubular in construction and wherein said leader is received within and affixed to said cord.

7. The flossing device as described in claim 4 wherein said floss leader and said flossing cord are constructed of nylon.

* * * * *